United States Patent [19]
Praud et al.

[11] Patent Number: 5,497,765
[45] Date of Patent: Mar. 12, 1996

[54] DEVICE FOR THE SIMULTANEOUS DELIVERY OF BETA-2 AGONISTS AND OXYGEN TO A PATIENT

[75] Inventors: Jean-Paul Praud; Sophie Baron, both of Sherbrooke; Mario Geoffroy, Stoke; Rachel Rouleau, Sacré-Coeur de Marie, all of Canada

[73] Assignee: RD-Chus Inc., Québec, Canada

[21] Appl. No.: 377,401

[22] Filed: Jan. 24, 1995

[30] Foreign Application Priority Data

May 26, 1994 [CA] Canada .................................. 2124410

[51] Int. Cl.⁶ .................................................. A61M 11/00
[52] U.S. Cl. .............................. 128/200.23; 128/203.25; 128/205.11
[58] Field of Search ...................... 128/200.14, 200.23, 128/203.25, 205.11

[56] References Cited

U.S. PATENT DOCUMENTS

| | | | |
|---|---|---|---|
| 3,490,452 | 1/1970 | Greenfield | 128/200.23 |
| 4,823,784 | 4/1989 | Bordoni et al. | 128/200.14 |
| 5,078,131 | 1/1992 | Foley | 128/200.14 |
| 5,178,138 | 1/1993 | Walstrom et al. | 128/200.23 |
| 5,320,094 | 6/1994 | Laube et al. | 128/200.23 |

*Primary Examiner*—Aaron J. Lewis
*Attorney, Agent, or Firm*—Robic

[57] ABSTRACT

A device for the simultaneous delivery of beta 2 agonists and oxygen to a patient. This device comprises a main chamber, an adaptor at one end of the chamber to accomodate a metered dose inhaler, and a mask or mouthpiece detachably mounted at the other end of the main chamber. A tube of given length is connected to and in open communication with the main chamber at one end, and open to air at the other end. A unidirectional valve is placed in the tube at a short distance from the end connected to the main chamber mounted in such a manner as to allow flow circulation within the tube towards the main chamber exclusively. An auxiliary tube is connected to and in open communication with the tube at one end, at a given distance from the unidirectional valve away from the main chamber. The other end of this auxiliary tube is devised to accomodate an oxygen source.

10 Claims, 2 Drawing Sheets

DEVICE FOR THE SIMULTANEOUS DELIVERY OF BETA-2 AGONISTS AND OXYGEN TO A PATIENT

BACKGROUND OF THE INVENTION

A) Field of the Invention

The present invention is concerned with a device for the simultaneous delivery of beta 2 agonists and oxygen to a patient.

B) Brief Description of Prior Art

Oxygen and beta 2 agonists are two basic medications for treating asthma in an emergency room. Usually, oxygen is administered directly to the patient through a mouthpiece or a face mask while beta 2 agonists are administered in the patient's throat with a metered dose inhaler. When the beta 2 agonists are administered, the mouthpiece or face mask must be removed, thereby reducing the efficiency of the treatement, specifically, maintaining normoxia.

Recently, it has been shown that beta 2 agonist administration is particularly effective when a metered dose inhaler is used in conjunction with a spacer, like the one sold by Trudell Medical, London, Ontario, Canada under the trade mark Aerochamber. However, the inability to deliver oxygen while using a metered dose inhaler with a spacer has been criticized. The present invention offers the possibility of administering beta 2 agonists and oxygen simultaneously, through a set of tubes connected to and in open communication with a spacer.

OBJECT AND SUMMARY OF THE INVENTION

Thus, the object of the present invention is to provide a device for the simultaneous delivery of beta 2 agonists and oxygen, particularly to a patient in an emergency room, which comprises a spacer, hereinafter called "main chamber", and a set of tubes connected to the chamber for feeding oxygen to the patient through the chamber, thereby permitting delivery of oxygen while using a metered dose inhaler.

In accordance with the invention as broadly claimed hereinafter, this object is achieved with a device comprising, in combination:

(a) a main chamber, having a longitudinal axis and a pair of opposite ends;

(b) an adaptor at one end of the opposite ends of the main chamber, hereinafter called "inhalor end", to accomodate a metered dose inhaler;

(c) a mask or mouthpiece detachably mounted at the other end of the main chamber, hereinafter called "patient end";

(d) a tube of given length, having a longitudinal axis and a pair of opposite ends, one of the opposite ends being connected to and in open communication with the main chamber at a given distance from the inhaler end, the other one of the opposite ends being open to air; this tube also includes a unidirectional valve at a short distance from the end connected to the main chamber mounted in such a manner as to allow flow circulation within the tube towards the main chamber exclusively;

(e) an auxiliary tube having a longitudinal axis and a pair of opposite ends, one of the opposite ends being connected to and in open communication with the tube, at a given distance from the unidirectional valve away from the main chamber, the other of the opposite ends being able to accomodate an oxygen source.

In use, when the patient inhales deeply through the mask or mouthpiece, oxygen fed into the tube through the auxiliary tube enters the main chamber through the unidirectional valve and thus can be inhaled by the patient. When a metered dose of beta 2 agonists is sprayed towards the mask or mouthpiece through the main chamber for inhalation by the patient, such dose is prevented from escaping through the tube thanks to the unidirectional valve; when the patient inhales through the mask or mouthpiece, the unidirectional valve opens to permit the beta 2 agonists and the oxygen to mix and be simultaneously inhaled by the patient. If no metered dose of beta 2 agonists is sprayed, the patient will nonetheless still be able to inhale oxygen. When the patient is not inhaling, the oxygen exits the tube through the end that is open to air.

The invention and its advantages will come much more apparent from the following non-restrictive description of a preferred embodiment thereof, given with reference to the accompanying drawings.

DESCRIPTION OF A PREFERRED EMBODIMENT

Figure 1:
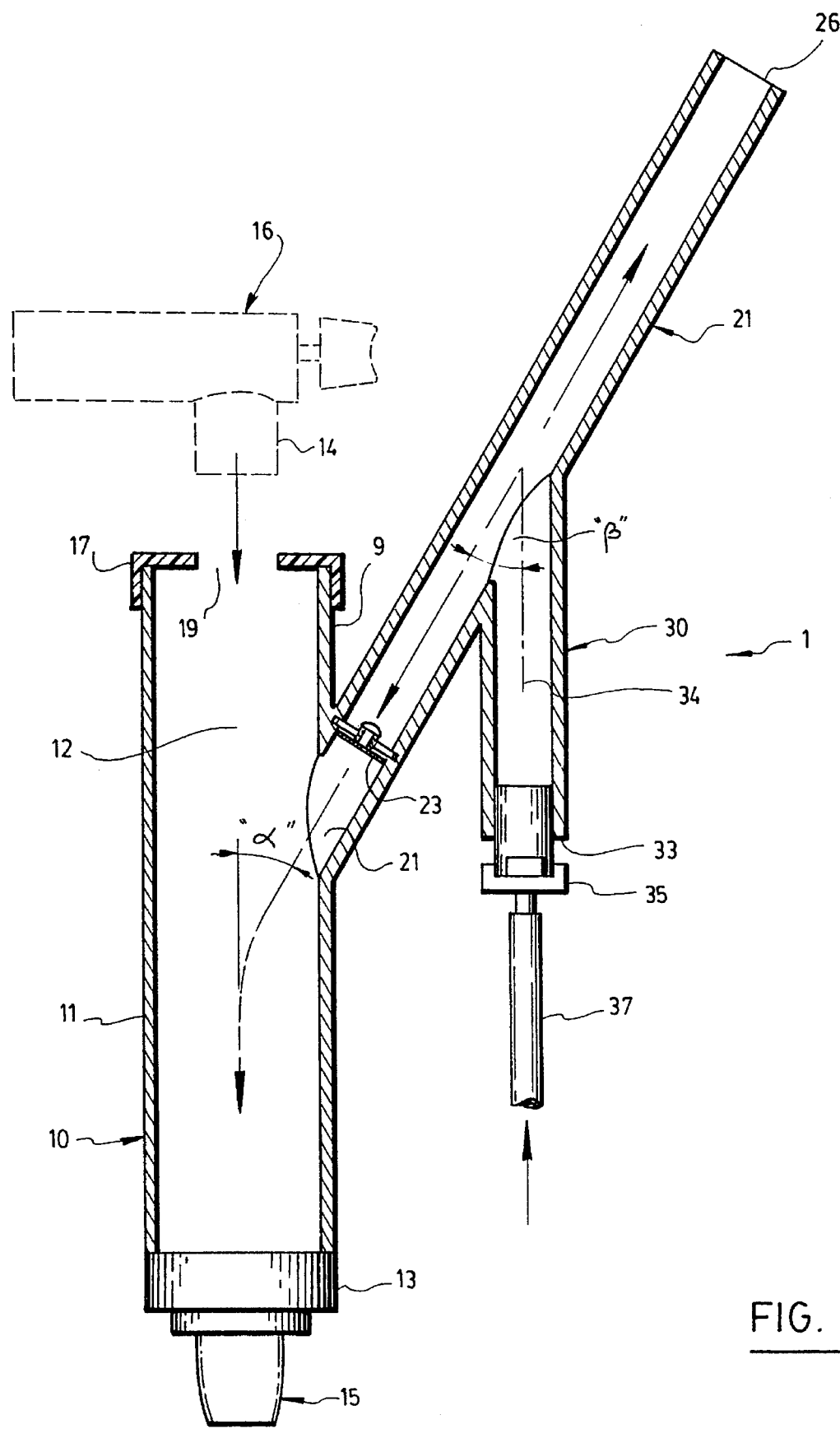
FIG. 1 is a cross-sectional top plan view of a device according to a preferred embodiment of the invention.

The device 1 according to the invention as shown in the accompanying drawings is intended to be used for simultaneously delivering beta 2 agonists and oxygen to a patient. It comprises in combination: a main chamber 10, a tube 20 and an auxiliary tube 30, each of which are preferably cylindrical.

Figure 2:
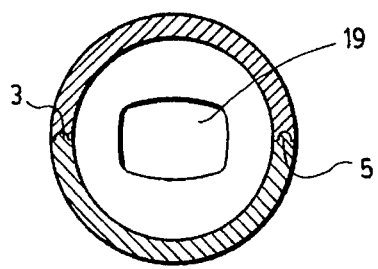
FIG. 2 is a cross-sectional view of the main cylindrical chamber taken along line II—II.

All these components preferably lie in a same plane, as shown in FIG. 1. In such case, the main cylindrical chamber 10, the cylindrical tube 20 and the auxiliary cylindrical tube 30 are preferably made of two interlocking pieces, symmetrical with respect to the plane, one of the pieces having a grooved edge 3 sized to fit into tongues 5 provided in the other piece, as can be seen from FIG. 2.

Furthermore, as can be seen in FIG. 1, the tube 20 extends at an angle α with respect to the main chamber 10 in a direction away from the patient end 7 and the auxiliary tube 30 extends at an other angle B with respect to the tube 20 in the same direction as the unidirectional valve 23. Preferably, both angles will be identical and equal to about 30° to prevent washout of the main chamber content by the oxygen flow.

As shown in FIG. 1, the main cylindrical chamber 10, is defined by a body 11, which may have a volume of about 145 mL, and two opposite ends.

As clearly shown in FIG. 1, the body 11 of the main cylindrical chamber 10 has one end 9, hereinafter called "inhalor end", on which a rubber adaptor 17 is fitted. This adaptor has a central opening 19, which is better shown in FIG. 2, and is designed and sized to accomodate the delivery mouth 14 of a metered dose inhalor 16 of conventional structure.

Figure 4:
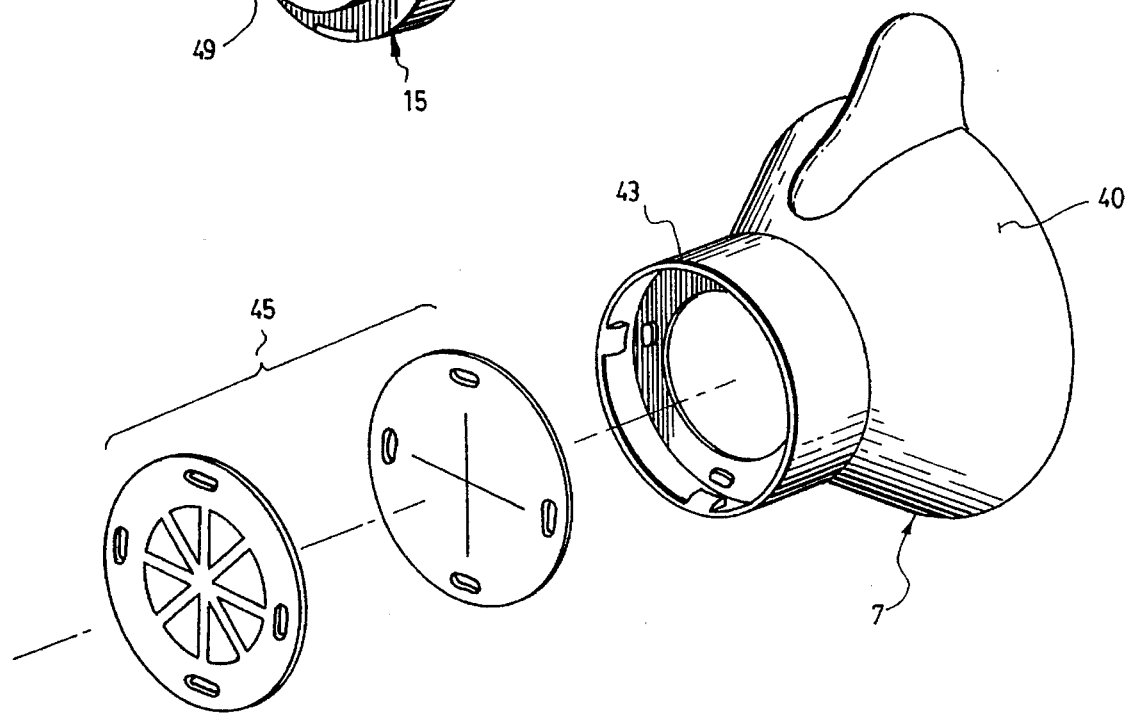
FIG. 4 is an exploded perspective view of a mouthpiece and check valve for use as a substitute for the mouthpiece shown in FIG. 3.

The other end 13, hereinafter called "patient end", is slightly narrower than the body in order to accomodate a mouthpiece 15 or, as shown in FIG. 4, a mask 7, which will be described in greater detail below.

The cylindrical tube 20 has two opposite ends. One of them is attached to and in open communication 21 with the main cylindrical chamber 10. The other end 26 is open to air. This cylindrical tube 20 includes a unidirectional valve 23, positioned near the main chamber 10 so as to permit gas flow towards the main cylindrical chamber 10 exclusively when the patient inhales through the mouthpiece 15 or mask 7.

Preferably, the length and diameter of the cylindrical tube 20 are selected so that the tube 20 contains a given volume of oxygen, which may vary depending on the patient's morphology. For example, the size for an adult would be 7½ inches in length and ½ inch in diameter, whereas for a child or infant, the length would be reduces to 4 inches.

The auxiliary cylindrical tube 30 has two opposite ends. One of them is connected to and in open communication 31 with the cylindrical tube 20. An oxygen tube 37 can be connected either directly or via an air-oxygen mixer 35 to the other end 33. Such mixer is known per se and can be used to adjust the respective amounts of pure oxygen and air to be delivered to the auxiliary cylindrical tube.

As can be seen in FIG. 4, the mask 7 has two ends, one of which 40 fits over the nose and mouth of a patient, the other end 43 snapping onto the narrow end 13 of the main cylindrical chamber 10. Preferably, a check valve 45 is inserted between the mask 7 and the narrow end 13 of the main cylindrical body 10, so that when the metered dose inhaler 16 is activated, the beta 2 agonists do not enter directly into the mouth of the patient.

Figure 3:
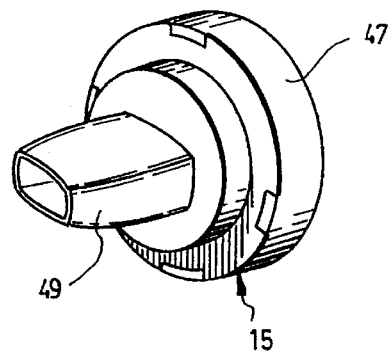
FIG. 3 is an exploded perspective view of a mouthpiece for use with the device shown in FIG. 1.

Similarly, as shown in FIG. 3, the mouthpiece 15 also has two ends. One 47 of these ends is designed to snap-fit on to the narrow end 13 of the main cylindrical body. The other end 49 is open and shaped to fit into the mouth of the patient so that the patient may inhale through this opening. A check valve like the one shown in FIG. 4 can be mounted between the mouthpiece 15 and the main cylindrical body 10.

In use, when the patient inhales deeply through the mask 7 or mouthpiece 15, oxygen fed into the tube 20 through the auxiliary tube 30 enters the main chamber 10 through the unidirectional valve 23 and thus can be inhaled by the patient. When a metered dose of beta 2 agonists is sprayed towards the mask 7 or mouthpiece 15 through the main chamber 10 for inhalation by the patient, such dose is prevented from escaping through the tube 20 thanks to the unidirectional valve 23; when the patient inhales through the mask 7 or mouthpiece 15, the unidirectional valve 23 opens to permit the beta 2 agonists and the oxygen to mix and be simultaneously inhaled by the patient. If no metered dose of beta 2 agonists is sprayed, the patient will nonetheless still be able to inhale oxygen. When the patient is not inhaling, the oxygen exits the tube 20 through the end 26 that is open to air.

The embodiments of the invention in which an exclusive property or privilege is claimed are as follows:

1. A device for the simultaneous delivery of beta 2 agonists and oxygen to a patient, said device comprising:

(a) a main chamber, having a longitudinal axis and a pair of opposite ends;

(b) an adaptor at one end of the said opposite ends of the chamber, hereinafter called "inhalor end", to accomodate a metered dose inhaler;

(c) a respiratory element selected from the group consisting of masks or mouthpieces, said element being detachably mounted at the other end of said opposite ends, hereinafter called "patient end";

(d) a tube of given length, having a longitudinal axis and a pair of opposite ends, one of said opposite ends being connected to and in open communication with said main chamber at a given distance from said inhaler end, the other one of said opposite ends being open to air, said tube including a unidirectional valve at a short distance from the end connected to the main chamber, said unidirectional valve being mounted in such a manner as to allow flow circulation within said tube towards main chamber exclusively;

(e) an auxiliary tube having a longitudinal axis and a pair of opposite ends, one of said opposite ends being connected to and in open communication with said tube, at a given distance from said unidirectional valve away from said main chamber, the other of said opposite ends being able to accomodate an oxygen source;

whereby, in use:

when the patient inhales through said respiratory element, oxygen fed into said tube through said auxiliary tube enters said main chamber through said unidirectional valve and thus can be inhaled by the patient, and when a metered dose of beta 2 agonists is sprayed towards said respiratory element through said main chamber for inhalation by the patient, said metered dose is prevented from escaping through said tube thanks to said unidirectional valve which opens only to permit said metered dose of beta 2 agonists and said oxygen to be mixed and be simultaneously delivered to the patient during inhalation.

2. A device according to claim 1 wherein said tube extends at an angle with respect to said main chamber in a direction away from said patient end and said auxiliary tube extends at an other angle with respect to said tube in the same direction as said unidirectional valve.

3. A device according to claim 2 wherein said angle and said other angle are identical and equal to about 30°.

4. A device according to claim 2 wherein said respiratory element is a mask designed to fit over the nose and mouth of the patient.

5. A device according to claim 4 wherein said mask includes a check valve.

6. A device according to claim 2 wherein said respiratory element is a mouthpiece.

7. A device according to claim 6, wherein said mouthpiece includes a check valve.

8. A device according to claim 2 wherein said tube is sized to provide a given volume of oxygen on each inhalation.

9. A device according to claim 8 wherein said main chamber, said tube and said auxiliary tube extend in the same plane and said device is made of two intelocking pieces symmetrical with respect to said plane, one of the pieces having grooved edges sized to fit into tongues provided in the other of the said pieces.

10. A device according to claim 9 wherein said device is made of plastic material and said adaptor is made of a rubber composite.

\* \* \* \* \*

UNITED STATES PATENT AND TRADEMARK OFFICE
CERTIFICATE OF CORRECTION

PATENT NO. :     5,497,765

DATED      :     March 12, 1996

INVENTOR(S) :    Jean-Paul PRAUD et al.

It is certified that error appears in the above-identified patent and that said Letters Patent is hereby corrected as shown below:

Column 2, line 52: "7" should read --13--;

Column 3, line 19: "communication 31" should read --communication--.

IN THE DRAWINGS:

On Figure 1, numeral "21" on the top right-hand side of the Figure should read --20--.

Signed and Sealed this

Thirtieth Day of July, 1996

Attest:

BRUCE LEHMAN

Attesting Officer        Commissioner of Patents and Trademarks